United States Patent [19]

Koprowski et al.

[11] 4,349,528
[45] Sep. 14, 1982

[54] MONOCOLONAL HYBRIDOMA ANTIBODY SPECIFIC FOR HIGH MOLECULAR WEIGHT CARCINOEMBRYONIC ANTIGEN

[75] Inventors: Hilary Koprowski, Wynnewood; Kenneth F. Mitchell, Unionville; Zenon Steplewski, Strafford, all of Pa.

[73] Assignee: The Wistar Institute, Philadelphia, Pa.

[21] Appl. No.: 96,309

[22] Filed: Nov. 21, 1979

[51] Int. Cl.³ .................. G01N 56/00; G01T 1/00
[52] U.S. Cl. .......................... 424/1; 424/12; 424/85; 23/230 B; 435/41
[58] Field of Search .............. 424/1, 9, 12, 85; 435/41; 23/230 B

[56] References Cited

U.S. PATENT DOCUMENTS

| | | | |
|---|---|---|---|
| 3,663,684 | 5/1972 | Freedman | 424/1 |
| 3,697,638 | 10/1972 | Hansen | 424/1 |
| 3,852,415 | 12/1974 | Vandervoode | 424/1 |
| 3,867,363 | 2/1975 | Hansen | 424/1 |
| 4,098,876 | 4/1978 | Piasio | 424/1 |
| 4,140,753 | 2/1979 | Edgington | 424/1 |
| 4,172,124 | 10/1979 | Koprowski et al. | 424/85 |
| 4,180,499 | 12/1979 | Hansen | 424/1 |

OTHER PUBLICATIONS

Welsh, Nature, vol. 266, Apr. 7, 1977, p. 495.
Simpson, Nature, vol. 272, Apr. 27, 1978, pp. 751–752.
Koprowski et al., Proc. Natl. Acad. Sci., USA, vol. 74, No. 7, Jul. 1977, pp. 2985–2988.
Herlyn et al., Proc. Natl. Acad. Sci., USA, vol. 76, No. 3, pp. 1438–1442, Mar. 1979.
Accolla et al., Proc. Natl. Acad. Sci., USA, vol. 77, pp. 563–566, Jan. 1980.

*Primary Examiner*—Christine M. Nucker
*Attorney, Agent, or Firm*—Schuyler, Banner, Birch, McKie & Beckett

[57] ABSTRACT

It has been determined that 180,000 dalton molecular weight carcinoembryonic antigen has an antigen site which is not shared by other molecular weight carcinoembryonic antigens, which are released by colorectal carcinoma. A hybridoma antibody specific for the 180,000 dalton molecular weight carcinoembryonic antigen is described.

4 Claims, No Drawings

MONOCOLONAL HYBRIDOMA ANTIBODY SPECIFIC FOR HIGH MOLECULAR WEIGHT CARCINOEMBRYONIC ANTIGEN

The invention described herein was made in the course of work under a grant or award from The Department of Health and Human Services. The substance now known as carcinoembryonic antigen (CEA) was first described by Gold and Freeman (J. Exp. Med. 121: 439–462, (1965); J. Exp. Med. 122: 467–481, (1965)). CEA was, at first, believed to be diagnostic for the presence of colorectal carcinoma but subsequently it was shown to be present in patients with a variety of other conditions (Proc. Nat. Acad. Sci. USA 64: 161–167, (1969); New Engl. J. Med. 285: 138–141, (1971); Amer. J. Dig. Dis. 16: 1–7, (1971); Immunochemistry 10: 197–204, (1973); Hum. Path: 5 139–147, (1974)). Classically xeno-antisera have been used to detect the presence of, and measure the levels of, CEA (Hum. Path: 5 139–147, (1974)) but studies on the structure of CEA have shown that a variety of different molecular species may be detected by any particular antiserum (Immunochem 14: 119–127, (1977); Br. J. Cancer 36: 446–452, (1977); J. Nat. Cancer Inst., (In press)).

The stability and solubility of CEA in the presence of perchloric acid has been utilized for the purification of CEA from tumor tissues (Immunochemistry 39: 377–387, (1972)). The CEA molecule is reported to contain 40–70% carbohydrate (Dent PB, Carrel S, Mach J-P: Detection of new cross reacting antigens on cultured tumor cells by mixed hemadsorption assay. J Nat Cancer Inst, (In press)) and to have molecular weights which range from about 125,000 to about 300,000 (Immunochemistry 39: 377–387, (1972); Scan J Immun (Suppl), 8(8): 423–428. (1978)). Highly purified CEA-S (generally regarded to have a molecular weight of about 180,000 daltons and a restricted heterogeneity) has been reported to have a higher diagnostic value as test for colorectal carcinoma (Int J Cancer: 748–761, (1975); Fed Proc 34: 845, (1975)).

The studies discussed above have all utilized antisera which were, of necessity, absorbed with suitable normal cross reactive tissues and antigens to remove antibodies reactive with blood group substances and other entities. Such procedures, however, are not adequate to avoid at least some heterogeneity of antibodies.

It is an object of this invention to provide an antibody with reactivity directed specifically to carcinoembryonic antigen having a molecular weight of about 180,000 daltons.

It is a further object of this invention to provide a hybrid cell which produces a monoclonal antibody with reactivity directed specifically to carcinoembryonic antigen having a molecular weight of about 180,000 daltons.

It is an additional object of this invention to provide a diagnostic test for carcinoembryonic antigen employing the antibody of this invention.

In accordance with this invention there is provided a monoclonal hybrid cell (hybridoma) which produces an antibody with reactivity directed spcifically to carcinoembryonic antigen having a molecular weight of about 180,000 daltons. The invention also includes the antibody produced by the hybrid cell and the method of testing for the cancinoembryonic antigen. The hydridoma of this invention has been deposited with the American Type culture collection and is assigned ATCC #CRL-8019.

As noted above, commercial CEA contains several components of varying molecular weight and goat antisera does not differentiate among them. Indeed, another hybridoma (other than the hydridoma of this invention) formed from the spleen cells of mice immunized with SW1116, a CEA excreting cell, similarly precipitates molecules of several sizes from $^{125}$I-CEA even through the hybridoma produced only a single antibody. According to this invention it has been determined that 180,000 molecular weight CEA has an antigen site not shared with other molecular weight components of CEA and an antibody has been discovered which is specific for that antigen site. Moreover, the antibody of this invention, while reactive for all colorectal carcinoma cells tested, has not been reactive with normal cells or cells of other types of tumor. The ability of the hybridoma antibody of this invention to react specifically with the 180,000 molecular weight form of CEA provides a basis for an assay with exquisite specificity.

The general method used for production of antibody-secreting somatic cell hybrids has been previously described in Proc. Natl Acad Sci USA 75: 3405–3409, (1978) and in Koprowski U.S. Pat. No. 4,172,124, entitled "Method of Producing Tumor Antibodies".

Briefly, a BALB/c mouse was immunized with CEA excreting colorectal carcinoma cells from cell line SW1116 (obtained from the Scott and White Clinic, Temple, Tex.—cells from that source are designed SW) and spleen cells from this mouse were fused with nonsecretor myeloma cells of cell line P3×63 Ag8, variant 653, (Kearney et. al.: A New Mouse Myeloma Cell Line Which Has Lost Immunoglobulin Expression But Permits The Construction Of Antibody Secreting Hybridomas; J Immunol, 123, 1548–1550 (1979). More particularly, BALB/c mice were immunized for a secondary response as described in J Exp Med 121: 439–462, (1965). Three days prior to their sacrifice the mice were given a second injection intravenously of $1 \times 10^6$ immunizing cells (SW1116). After sacrifice, a spleen cell suspension was prepared in the manner described in Proc. Natl Acad Sci USA 74: 2985–2988 (1977). Immune splenocytes were fused with the variant 653 of the myeloma cell line P3×63 Ag8 in the presence of polyethylene glycol as also described in Proc. Natl Acad. Sci USA, 74 2985–2988 but with one variation. Prior to fusion, cells were washed in $Ca^{++}$ and $Mg^{++}$ free medium, and the fusion was performed in the absence of Ca and Mg ions.

Hybrids were selected in a medium which contained hypoxanthine/aminopterin/thymidine (HAT selective medium) (Science 145, 709–10, 1964) and fused cells were seeded in wells of 24 well tissue culture plates (Linbro FB-16-24TC). Approximately 20 days after fusion, single colonies were picked from each well and processed as described in Proc Natl Acad Sci USA 76: 1438–1442 (1979). The hybrid of this invention was informally designated 1116NS-3d but, as noted above, has now been deposited as ATCC #CRL-8019.

The hybridoma cells can be grown in vitro to produce the antibodies of this invention which are secreted by the cells into the medium. Any of a variety of known media can be employed, and the choice of a medium is easily within the skill of the art. One particularly satisfactory medium is Dulbecco's minimal essential medium (MEM) containing about 20% fetal calf serum.

Desireably, the medium chosen will be substantially free of antibodies so that purification steps to remove unwanted antibodies can be avoided.

In a typical procedure MEM+20% fetal calf serum is innoculated with the hybridoma cells of this invention and incubated at about 37° C. After a suitable period, for example 4 or 5 days, the liquid containing secreted antibodies is separated from the cells by centrifugation or the like. If desired, the cells can be added to fresh media to produce additional antibodies. The separated liquid can be used as such for analytical tests. If desired, however, the liquid can be subjected to any of the variety of purification steps known to the art. Indeed, procedures are well known to isolate the antibody of this invention if such is desired.

As noted above, CEA is secreted by colorectal carcinoma cells. For diagnostic purposes, the antibody of this invention is added to blood serum of serum extract and the reactivity of the antibody with the antigen is measured. Any of a variety of known antigen assay techniques may be used to measure the reactivity. In one such procedure the following steps are employed: (1) add an aliquot of antibody to $^{125}I$-CEA, agglutinate the bound material and determine counts of bound material; (2) Repeat (1) but in presence of added serum. More particularly, (1) an aliquot of 180,000 dalton molecular weight $^{125}I$-carcinoembryonic antigen is contacted with the antibody of this invention and (2) a second aliquot of 180,000 molecular weight $^{125}I$-carcinoembryonic antigen is mixed with blood serum to be tested and the mixture is contacted with an equal quantity of the antibody of this invention. In each case, the antibody (together with bound materials) is agglutinated, for example, by anti-mouse immunoglobulin. The radioactivity of the bound material from each step is measured and compared. A decrease in bound counts greater than normal variation among replicates of step (1) indicates the presence of CEA. A quantitative indication of the amount of 180,000 dalton molecular weight CEA in the blood serum can be obtained by comparing counts with those obtained for controls employing known amounts of non-radiolabeled CEA mixed with $^{125}I$-CEA. Other diagnostic procedures are also within the skill of the art.

Tissue culture supernatants containing the antibody of this invention were tested for binding to various tissue cultured cells. These included the determination of the reactivity of antibodies with radioiodinated colorectal carcinoma and other cells, determination of reactivity of antibodies with commercial CEA, determination of molecular weights of components, and determination of blocking of binding sites by different antibodies. For ease of presentation, the method of preparation of various components of the tests as well as various test procedures will be summarized and the test results will then be reported.

Radioiodination of Colorectal Carcinoma Cells: Cell surfaces were radiolabeled with iodine 125 by the lactoperoxidase method as described in Biochem J, 124, 921-927, (1971). Adherent monolayers of colorectal carcinoma cells were labeled in situ. Cells, as in situ layers in Falcon T25 flasks were washed twice with phosphate-buffered saline and then overlaid with 1 ml of phosphate-buffered saline (PBS) which contained 50 ug of lactoperoxidiase and 8 ug of glucose oxidase. 500 uCi of $^{125}I$ sodium iodide (NEN, Boston, MA) and 500 ul of 10 mM glucose were then added together with 5 nMoles of $^{127}I$ sodium iodide. Iodination was allowed to proceed for 15 minutes at room temperature and was terminated by washing the cell monolayer with PBS.

Radiolabeled cells were washed three times with PBS and solubilized by incubation for 15 min at 4° C. in 1 ml of NET buffer (0.15 M NaCl, 0.05 M TRIS, 5 mM EDTA, 0.2 mM phenylmethylsulphonyl fluoride, pH 7) containing 0.5% NP-40 (Shell Chemical Co., London, England). Solubilized material was centrifuged at 100,000 ×g for 30 min and absorbed serially with two 0.5 ml volumes of packed *Staphylococcus aureus* Cowan I (SaCI) previously washed with NET buffer containing 0.05% NP-40 and 1 mg/ml bovine serum albumin (BSA) (Pentex, Miles Laboratories, Inc., Elkhart, Ind. SaCI-cleared preparations (cleared of nonspecifically binding materials) were stored at −70° C. Precipitation of antigens: Aliquots of cleared radioiodinated cell lysates were mixed with 100 ul volumes of hybridoma tissue culture supernatant and incubated for 30 minutes. This mixtue was then added to a 50 ul pellet of SaCI (described below) previously coated with rabbitantimouse immunoglobulin (250 ug of rabbit anti-mouse Ig per 50 ul SaCI). The pellet was then suspended and, after a further 30 minute incubation, was centrifuged at 10,000 g for 5 minutes. Antigens were eluted from the SaCI complexes by treatment with Laemmli sample buffer as disclosed in Nature, 227: 680–685, (1970).

Iodinated CEA: A commercially available CEA assay kit was purchased from Hoffmann La Roche and the radio iodinated CEA ($^{125}I$-CEA) contained therein used for the experiments described below. The CEA is supplied in a sodium borate buffer containing 10% human plasma (blood group A).

Precipitation of iodinated CEA by Hoffmann La Roche goat anti CEA antiserum: Aliquots of iodinated CEA were incubated with goat anti-CEA by the method described in the CEA assay kit. No competitive cold CEA (i.e., not radioactive) was added and the antigen antibody complexes were precipitated by the addition of Z-gel (Zirconyl phosphate gel, Hoffmann La Roche). Precipitates were washed as described in the method and bound counts bound were determined by use of a Packard Autogamma Spectrometer.

Precipitation of iodinated CEA by hybridoma antibody: Immune complexes of hybridoma antibody with iodinated CEA were precipitated by two methods:

Method 1. Aliquots of iodinated CEA were mixed with hybridoma antibody and the reaction was allowed to proceed for 30 minutes. Rabbit anti-mouse immunoglobulin was then added, at equivalence, and after an overnight incubation complexes were recovered by centrifugation.

Method 2. A solid immunoabsorbent was prepared by incubation of plastic microbeads coated with goat anti-mouse immunoglobulin with hybridoma antibody. The hybridoma antibody coated beads were incubated with aliquots of $^{125}I$-CEA and, after 3 washes, the bound counts were measured as described above.

Determination of Molecular Weights: Molecular weights were determined by sodium dodecylsulphate-polyacrylamide gel electrophoresis (SDS-PAGE), as described by Laemmli in, Nature, 227: 680–685, (1970). Dissolved antigens were electrophoresed on 10% polyacrylamide SDS gels (acrylamide-bis ratio 38: 1). Electrophoresis was performed at a current of 20 mA until the dye front had traveled 10 cm. Apparent molecular weights of precipitated antigens were determined by comparison of the mobilities of the observed bands with the mobilities of a set of proteins whose molecular weights have been well characterized.

Tests regarding blocking of hybridoma antibody binding by anti-CEA antiserum: Radio iodinated CEA was mixed with goat anti-CEA and the reaction was allowed to equilibrate by incubation at 4° C. for 96 hours. Hybridoma antibody was then added and the mixture incubated at 37° for 30 minutes. Mouse immunoglobulin was precipitated by addition of the solid phase anti-mouse Ig immunoabsorbent described above. The mixture was incubated for 10 minutes at room temperature and the absorbent was centrifuged, washed and the amount of $^{125}I$ bound determined by gamma counting. Appropriate controls were performed with a non-specific mouse immunoglobulin.

Determination of nature of molecules detected by hybridoma antibody: A sample of iodinated CEA was incubated with a solid immunoabsorbent, as described, above, prepared either from hybridoma antibody or from a control non-specific monoclonal antibody (the protein produced by the cell line P3×63 AG8). After incubation the unbound constituents were recovered and the pellets were washed 3 times. The bound materials were eluted with SDS sample buffer (Nature 227: 680–685, (1970)) and, together with the unbound material, subjected to SDS-PAGE.

Direct binding radioimmunossays: All assays were performed according to the procedure described in Proc. Natl. Acad. Sci. USA 75: 3405–3409, (1978). Target cells ($5 \times 10^5$) were incubated with the hybridoma antibody for 1 hour at room temperature. The cells were washed three times and then incubated with radiolabeled ($^{125}I$) rabbit antimouse F(ab')$_2$. After three final washes, the amount of radioactivity present in the pellet was assessed by counting in a Packard gamma spectrometer.

The antibody of this invention detected CEA from a colorectal carcinoma cells. Immune complexes were formed between the hybridoma antibody of this invention and radio-iodinated, solubilized, cleared, SW948 colorectal carcinoma cells (obtained from Scot and White Clinic). Complexes, recovered by binding to rabbit antimouse immunoglobulin coated SaCl were solubilized in SDS sample-buffer and subjected to SDS-PAGE analysis. A dense radioactive band was formed in the upper region of the gel that had a molecular weight of 180,000 daltons. Similar bands of varying intensities were seen in preparation from other colorectal carcinoma cell lines. Control antibody, P3, did not precipitate the 180,000 molecular weight antigen.

The antibody of this invention was tested for reactivity with carcinoma and other cell lines. Importantly, it bound to all eight colorectal cell lines tested but did not bind to any of 23 other cell lines tested. More particularly, it did not bind to any of 3 lung carcinoma cell lines, 1 breast carcinoma cell line, 10 melanoma cell lines, 2 astrocytoma cell lines, 2 sarcoma cell lines or to 5 fibroblasts, (1 SV40 transformed, 2 fetal and 2 adult).

The reactivity of a hybridoma supernatant containing the antibody of this invention with eight colorectal carcinoma cell lines was measured by the radioimmunoassay described above and the results are shown in Table I.

As Table I demonstrates, the antibody was reactive with all eight cell colorectal carcinoma cell lines. (Background counts as measured by binding to non-colorectal cell lines are at most 250 cpm).

The reactivity of the antibody of this invention was also demonstrated with respect to commercial CEA. Aliquots of the hybridoma culture supernatant of this invention were incubated for varying periods of time with $^{125}I$-CEA. Immune complexes were precipitated, either by overnight incubation with rabbit anti-mouse Immunoglobulin (method 1) or by a 10 minute incubation with an insoluble goat anti-mouse immunoglobulin (Ig) (method 2.) Results are presented in Table II and show that the antibody of this invention precipitates only 10% of the commercial iodinated CEA preparations. In contrast goat anti-CEA precipitates 60% of the iodinated materials. Precipitation with increased amounts of monoclonal hybrid antibody on prolongation of the incubation period did not increase the amount of iodinated material precipitated.

TABLE II

| ANTIBODY | INCUBATION TIME | PRECIPITATION METHOD | COUNTS PRECIPITATED (%) |
|---|---|---|---|
| P3 | ON* | 1 | 2 |
| Monoclonal antibody of invention | ON | 1 | 10 |
| Goat-anti CEA | ON | 1 | 60 |
| P3 | 30 minutes | 2 | 2 |
| Monoclonal antibody of invention | 30 minutes | 2 | 10 |
| P3 | ON | 2 | 2 |
| Monoclonal antibody of invention | ON | 2 | 10 |

*overnight

Tests were also conducted that demonstrate that the antibody of this invention did not attach to the same antigenic site as goat anti-CEA antisera. 25 ul samples of $^{125}I$-CEA were preincubated with 100 ul or 1 ml volumes of goat anti-CEA for 96 hours prior to assay procedure which is described above. In the assay itself, samples of $^{125}I$-CEA and goat anti-CEA were mixed with aliquots of the monoclonal antibody of this invention. The results are presented in Table III and show that the presence of 100 ul of goat anti-CEA reduced the number of counts bound by the antibody of this invention by about 20%. However a ten fold increase in the amount of a goat-antibody did not increase the inhibitory effect. Therefore, the reduction in precipitation is considered to be due to a volume or steric effect rather than true competition for antigenic sites on the CEA molecule.

TABLE III

| VOLUME OF GOAT ANTI-CEA | MONOCLONAL ANTIBODY | COUNTS PRECIPITATED(%) |
|---|---|---|
| None | P3 | 2 |
| None | Invention | 10 |
| 100 ul | Invention | 8 |
| 100 ul | Invention | 8 |
| 1 ml | P3 | 2 |
| 1 ml | Invention | 8 |

*Preincubated together for 96 hours.

TABLE I

| Cell Line | SW1116 | SW1222 | SW1463 | SW403 | SW948 | SW1083 | SW837 | SW1345 |
|---|---|---|---|---|---|---|---|---|
| Assay(cpm) | 2987 | 5297 | 3387 | 873 | 763 | 1844 | 1212 | 2407 |

25 ul (40,000 cpm) of $^{125}$I-CEA was added to all tubes in the assay of Table III.

The material precipitated by the antibody of this invention was solubilized and subjected to SDS-PAGE. Iodinated CEA was also run as a standard for comparison together with $^{125}$I-CEA that had been extensively absorbed with the antibody of this invention or with P3. The results demonstrated that $^{125}$I-CEA has a significant heterogeneity in terms of molecular size and contains molecules of 180,000, 120,000, 110,000 and 60,000 daltons. In contrast, the antibody of this invention precipitates only molecules with a molecular weight of 180,000 daltons from this complex mixture. The materials which were not precipitated by the antibody of this invention still, in contrast, contained species with a wide range of molecular weights and included all the lower molecular weight species. P3 antibody did not precipitate any radiolabeled material.

The above results demonstrate that the antibody of this invention only precipitates antigens with a molecular weight of 180,000 daltons from iodinated colorectal carcinoma cells from iodinated commercial purified CEA. Second, the antibody does not precipitate the low molecular weight substances present in commercial iodinated CEA. Third, goat anti-CEA does not inhibit the binding of the antibody of this invention to its target antigen and, thus, the monoclonal antibody recognizes an antigen site on CEA not detected by the goat anti-CEA used in this study. These data suggest that the monoclonal antibody of this invention binds specifically to a determinant found only on the 180,000 dalton isomer of CEA. Since it has now been determined that an antibody exists which is specific for the 180,000 dalton molecular weight CEA, corresponding antibodies can be made from hybrid cells obtained from animals other than mice. For example a hybrid of mouse and rat could be used, as could any combination of cells so long as the cells of one species will fuse with the other. As used in the claims, the term "corresponding to" the antibody produced by hybridoma ATCC #CRL-8019 embraces antibodies which attach to the same site of the 180,000 dalton molecular weight CEA, and are not reactive with the other components of CEA. "Corresponding" antibodies, therefore, are those whose attachment to the 180,000 dalton molecular weight CEA is blocked by the antibody produced by ATCC #CRL-8019. Blocking may be determined by the use of 180,000 dalton molecular weight $^{125}$I-CEA using the known procedure described above.

Since variations of the invention will be apparent to those skilled in the art, it is intended that this invention be limited only by the scope of the appended claims.

We claim:

1. A diagnostic method for detecting the presence of colorectal carcinoma which comprises contracting blood serum with a monoclonal antibody having a specificity for 180,000 dalton molecular weight carcinoembryonic antigen and which corresponds to the antibody produced by hybrid cell ATCC #CRL-8019, and measuring materials bound by the antibody.

2. The method of claim 1 wherein
   (a) an aliquot of 180,000 molecular weight $^{125}$I-carcinoembryonic antigen is contacted with the antibody and the antibody is aggluntinated;
   (b) a second aliquot of 180,000 molecular weight $^{125}$I-carcinoembryonic antigen is mixed with blood serum and the mixture is contacted with the antibody and the antibody is aggluntinated; and
   (c) the radioactivity of the bound material of step (b) is compared with the radioactivity of the bound material step (a), a decrease in the radioactivity of bound material in step (b) indicating the presence of 180,000 carcinoembryonic antigen in the blood serum.

3. An antibody having a specificity for 180,000 dalton molecular weight carcinoembryonic antigen and corresponding to the monoclonal antibody produced by hybrid cell ATCC #CRL-8019.

4. The method of claim 1 wherein the monoclonal antibody is produced by hybrid cell ATCC #CRL-8019.

* * * * *